United States Patent [19]

Hugelshofer

[11] Patent Number: 4,910,026

[45] Date of Patent: Mar. 20, 1990

[54] STERILIZED WATER-INSOLUBLE MINERAL SALT AND PRODUCTS CONTAINING IT

[75] Inventor: Willy Hugelshofer, Konolfingen, Switzerland

[73] Assignee: Nestec S.A., Vevey, Switzerland

[21] Appl. No.: 168,251

[22] Filed: Mar. 15, 1988

[30] Foreign Application Priority Data

Mar. 31, 1987 [CH] Switzerland ........................ 1228/87

[51] Int. Cl.[4] ........................ A23L 1/20; A23C 9/137

[52] U.S. Cl. ........................ 426/74; 426/598; 426/580; 426/634; 426/656; 426/657; 426/573; 426/658; 426/521; 426/522; 426/800; 426/801

[58] Field of Search ............... 426/634, 598, 573, 578, 426/580, 74, 656, 657, 658, 521, 522, 800, 801, 578

[56] References Cited

U.S. PATENT DOCUMENTS

| | | | |
|---|---|---|---|
| 4,105,803 | 8/1978 | Peng | 426/634 |
| 4,514,433 | 4/1985 | Matsuura | 426/634 |

*Primary Examiner*—Marianne Cintins
*Attorney, Agent, or Firm*—Vogt & O'Donnell

[57] ABSTRACT

Water-insoluble salts are sterilized by heating them in suspension in water together with xanthum gum or carboxymethyl cellulose which is added for improving the homogeneity and stability of the salt suspension during heating. The salts are suspended in water and the gum or cellulose is added to the suspension which is heated to a temperature of from 120° C. to 150° C. for sterilizing it. The sterilized suspension may be utilized to improve the nutritional qualities of products and as a coagulating agent in sterilized products including milk, dietetic products and tofu and is particularly useful for aseptically packaged products.

14 Claims, No Drawings

STERILIZED WATER-INSOLUBLE MINERAL SALT AND PRODUCTS CONTAINING IT

BACKGROUND OF THE INVENTION

This invention relates to a process for sterilizing an aqueous suspension of a water-insoluble salt or salts for subsequent use in aseptic filling. The invention also relates to the use of this sterilized suspension.

Aseptic filling is known and provides for the preparation of products which keep for six months or more. This is particularly the case with milk. To improve the nutritional qualities of aseptically packed products, it would be interesting to add mineral salts to them. Now, numerous potentially usable mineral salts are insoluble in water. The solution which comprises directly adding these mineral salts to the product and then sterilizing the mixture obtained is not possible because it leads to a degraded end product as a result of secondary reactions during the sterilization process. Accordingly, separate sterilization should be considered for the basic product product and the mineral salts to be added. Now, the continuous sterilization of an aqueous suspension of an insoluble salt is virtually impossible in view of the heavy sedimentation of the salt, the covering of the heating and cooling surfaces and the abrasion of the pump components.

SUMMARY OF THE INVENTION AND DESCRIPTION OF PREFERRED EMBODIMENTS

The process according to the present invention enables an aqueous suspension of an insoluble salt to be sterilized without any of the disadvantages mentioned above. The invention relates to a process for sterilizing an aqueous suspension of a water-insoluble salt or salts for subsequent use in aseptic filling, in which a compound selected from the group comprising xanthan gum and carboxymethyl cellulose is added to the suspension which is then heated to a temperature in the range from 120° to 150°C.

Xanthan gum and carboxymethyl cellulose are thickeners which improve the homogeneity and stability of the suspension during the heat treatment without affecting the sterilized end product in any way.

The water-insoluble salt or salts is/are selected from the group comprising calcium, magnesium, iron, zinc and copper phosphate, citrate, sulfate and carbonate. One or other of these salts is introduced according to the desired objective. The content of salts in the suspension is from 0.1 to 10% by weight, based on the total weight of the suspension.

So far as the xanthan gum and the carboxymethyl cellulose are concerned, they are introduced in a quantity of 0.1 to 1% by weight, based on the total weight of the suspension.

The heat treatment of the suspension is carried out either indirectly using a plate or tube heat exchanger or directly using steam. After this treatment, the suspension is left to cool to a temperature of 20° to 80°C. It is thus ready for use either for making tofu or as an additive for milk or sterilized liquid dietetic products.

The starting material for the preparation of tofu or soya cheese is soya milk which is prepared in known manner as follows: the whole soya beans are washed with water and then immersed and soaked in water for a prolonged period. The soaking of the soya beans in water causes them to swell. The beans are then ground, crushed or pounded to form a puree or smooth, thick and white past. This paste or puree is heated and then filtered to give the soya milk. This milk is sterilized and then mixed with 1 to 20% by weight, based on the final total weight, of the sterilized suspension mentioned above and the mixture obtained is aseptically filled hot or cold. The function of the insoluble salt is to induce coagulation and precipitation of the tofu. The salt used in preferably calcium sulfate with xanthan gum. Other coagulating agents, such as $CaCl_2$, phytic acid and the like, may also be added to the sterilized suspension.

The sterilized suspension prepared in accordance with the invention may also be used as a mineral salt additive for milk or sterilized liquid dietetic products. In this case, 1 to 5% by weight, based on the final total weight, of this suspension is mixed with milk or sterilized liquid dietetic products and the mixture obtained is aseptically filled hot or cold. In the context of the invention, liquid dietetic products are understood to be both oral and enteral food compositions.

The type of salt used depends on the function which the beverage thus prepared is intended to fulfill. It is of course also possible to add soluble salts to the stabilized suspension.

EXAMPLES

The invention is illustrated by the following Examples relating to the preparation of tofu.

EXAMPLE 1

A soya milk having a total solids content of 13% is subjected to an ultra-high temperature treatment on an aseptic line. This heat treatment is applied for 2.4 seconds at a temperature of 150°C. The soya milk is then aseptically cooled. 5 kg $CaSO_4.2H_2O$ and 400 g xanthan gum (Keltrol F, a product of Kelco Co.) in 95 l water are then added to the suspension. The suspension is then heated to 135°C. in a plate-type heat exchanger and is kept at that temperature for 30 seconds. The suspension is then aseptically cooled to 30°C. The sterilized soya milk and the $CaSO_4$ suspension are continuously mixed before the filling process to form a mixture containing 92.5% soya milk and 7.5% $CaSO_4$ suspension. The mixture then passes to the aseptic filling line and the final pack is heated to coagulate to tofu in the aseptic container.

EXAMPLE 2

Soya milk is subjected to ultra-high temperature treatment on an aseptic line (5 seconds at 148°C.). The product leaves the UHT installation at 85°C., 6 kg $CaSO_4.2H_2O$ are added to 94 l cold water and 300 g xanthan gum (Keltrol F) are dissolved in the suspension. The stabilized suspension is heated at 140°C. for 10 seconds and then cooled to 85°C.

16 ml of the $CaSO_4$ suspension and, immediately afterwards, 184 ml hot soya milk are introduced into 200 ml containers in the aseptic filling machine. The tofu coagulates immediately and the filled containers merely have to be cooled before storage.

The invention thus provides a process by which a "longlife" tofu can be prepared with traditional coagulating agents.

I claim:

1. A process for sterilizing water-insoluble mineral salt comprising adding a compound selected from a group consisting of xanthum gum and carboxymethyl cellulose to an aqueous suspension of water-insoluble mineral salt for improving the homogeneity and stability of the salt suspension during heating and then heating the suspension to a temperature of from 120°C. to 150°C. for sterilizing the suspension.

2. A process according to claim 1 wherein the water-insoluble salt and the added compound are in an amount of from 0.1% to 10% and from 0.1% to 1%, respectively, by weight based upon the total weight of the suspension.

3. A process according to claim 1 or 2 wherein the salts are selected from a group consisting of calcium, magnesium, iron, zinc and copper phosphates, citrates, sulfates and carbonates.

4. A process for providing food products having added sterilized water-insoluble mineral salt comprising adding a compound selected from a group consisting of xanthum gum and carboxymethyl cellulose to an aqueous suspension of water-insoluble mineral salt for improving the homogeneity and stability of the salt suspension during heating, heating the suspension to a temperature of from 120°C. to 150°C. for sterilizing the suspension, cooling the sterilized suspension to a temperature of from 20°C. to 80°C. and then adding the cooled sterilized suspension to food products selected from a group consisting of sterilized soya milk, sterilized milk and sterilized liquid dietetic products.

5. A process according to claim 4 wherein the water-insoluble salt and the added compound are in an amount of from 0.1% to 10% and from 0.1% to 1%, respectively, by weight based upon the total weight of the suspension.

6. A process according to claim 4 or 5 wherein the product to which the cooled sterilized suspension is added is sterilized soya milk and wherein the cooled sterilized suspension is added in an amount of from 1% to 20% by weight based on total weight of the sterilized soya milk and added sterilized suspension.

7. A process according to claim 6 further comprising heating the sterilized soya milk and added sterilized suspension for coagulating a tofu from the sterilized soya milk and added suspension.

8. A process according to claim 6 wherein the cooled sterilized suspension is added to hot sterilized soya milk for coagulating a tofu from the sterilized soya milk and added suspension.

9. A process according to claim 6 wherein the salt is calcium sulfate and the compound is xanthum gum.

10. A process according to claim 4 or 5 wherein the products to which the cooled sterilized suspension is added are selected from the group consisting of sterilized milk and sterilized liquid dietetic products and wherein the cooled sterilized suspension is added in an amount of from 1% to 5% by weight based upon the total weight of the added sterilized suspension and the sterilized product to which it is added.

11. A process according to claim 6 wherein the salts are selected from a group consisting of calcium, magnesium, iron, zinc and copper phosphates, citrates, sulfates and carbonates.

12. A process according to claim 10 wherein the salts are selected from a group consisting of calcium, magnesium, iron, zinc and copper phosphates, citrates, sulfates and carbonates.

13. A process according to claim 4 or 5 wherein the product to which the cooled sterilized suspension is added is a sterilized dietetic product for enteral administration.

14. A process according to claim 4 or 5 further comprising aseptically packaging the food products having the added sterilized suspension.

* * * * *

UNITED STATES PATENT AND TRADEMARK OFFICE

CERTIFICATE OF CORRECTION

PATENT NO. : 4,910,026

DATED : March 20, 1990

INVENTOR(S) : Willy HUGELSHOFER

It is certified that error appears in the above-identified patent and that said Letters Patent is hereby corrected as shown below:

Column 4,line 1, (line 5 of claim 6), "on" should read --upon--.

Column 4,line 1, (line 5 of claim 6), insert --the-- before --total--.

Signed and Sealed this

Fifth Day of February, 1991

*Attest:*

HARRY F. MANBECK, JR.

*Attesting Officer* *Commissioner of Patents and Trademarks*